(12) United States Patent
Broderick et al.

(10) Patent No.: US 7,135,305 B2
(45) Date of Patent: Nov. 14, 2006

(54) METHODS FOR CONTROLLING THE LYSIS OF COAGULATED BLOOD WITH APOLIPOPROTEIN E4 PHENOTYPE

(76) Inventors: Joseph P. Broderick, MSB 4314 University of Cincinnati P.O. Box 670525, Cincinnati, OH (US) 45267-0525; Joseph F. Clark, Neurology Vontz 2326 University of Cincinnati P.O. Box 670525, Cincinnati, OH (US) 45267-0525; Daniel Woo, 8355 Miami Rd., Cincinnati, OH (US) 45243

( * ) Notice: Subject to any disclaimer, the term of this patent is extended or adjusted under 35 U.S.C. 154(b) by 472 days.

(21) Appl. No.: 10/398,882

(22) PCT Filed: Oct. 12, 2001

(86) PCT No.: PCT/US01/31909

§ 371 (c)(1),
(2), (4) Date: Jul. 17, 2003

(87) PCT Pub. No.: WO02/30454

PCT Pub. Date: Apr. 18, 2002

(65) Prior Publication Data

US 2004/0102374 A1    May 27, 2004

Related U.S. Application Data

(60) Provisional application No. 60/240,174, filed on Oct. 13, 2000.

(51) Int. Cl.
*C12Q 1/56* (2006.01)

(52) U.S. Cl. ................ 435/13; 424/94.64; 530/368.25
(58) Field of Classification Search .................. 435/6; 424/94.63, 94.64; 530/368.25
See application file for complete search history.

(56) References Cited

U.S. PATENT DOCUMENTS

| 6,046,381 A | 4/2000 | Mucke et al. |
| 6,313,089 B1 | 11/2001 | Matthew et al. |
| 2004/0006017 A1* | 1/2004 | Broderick et al. ............ 514/12 |

OTHER PUBLICATIONS

Friedman G. et al. Apo E4 Genotype Prdicts a Poor Outcome in Survivors of Traumatic Brain Injury. Neurology 1999, vol. 52, pp. 244-248.*
Shuvaev V., et al, Glycation of Apolipoprotein E Impairs Its Binding to Heparin: Identification of the Major Glycation Site. Biochimica et Biophysica Acta. Mar. 1999. vol. 1454, No. 3, pp. 296-308.

* cited by examiner

*Primary Examiner*—Ralph Gitomer
(74) *Attorney, Agent, or Firm*—Dinsmore & Shohl, LLP; Denise M. Everett

(57) ABSTRACT

Methods for inhibiting lysis of coagulated blood and reducing risk of excessive lysis comprising administration of lysis-inhibiting amounts of apolipoprotein E4, and methods for inhibiting lysis of coagulated blood and reducing risk of excessive lysis comprising administration of a specific level of a lysis-inhibiting agent wherein the specific level is based on the apolipoprotein phenotype of an individual, are provided. Methods for enhancing lysis of coagulated blood by administration of an Apo E peptide fragment to blood containing a clot lysis agent are also provided.

27 Claims, 5 Drawing Sheets

METHODS FOR CONTROLLING THE LYSIS OF COAGULATED BLOOD WITH APOLIPOPROTEIN E4 PHENOTYPE

RELATED APPLICATION

The present application is filed as a 371 application based on PCT/US01/31909 filed Oct. 12, 2001, which claims priority under 35 U.S.C. §119 to U.S. application Ser. No. 60/240,174 filed Oct. 13, 2000.

GOVERNMENT INTERESTS

This invention was made, at least in part, with funds from the Federal Government, awarded through NIH grants: NO1-NS-02382, NO1-NS-02374, NO1-NS-02377, NO1-NS-02379, NO1-NS-02373, NO1-NS-02378, NO1-NS-02376, NO1-NS-02380, and NIH RO1 HL67186-01. The US government therefore has certain acknowledged rights to the invention.

FIELD OF THE INVENTION

This invention relates to methods for inhibiting the lysis of coagulated blood and to methods for reducing the risk of excessive lysis by administration of a lysis-inhibiting amount of apolipoprotein E4. The invention further relates to methods for inhibiting the lysis of coagulated blood and to methods for reducing the risk of excessive lysis by the administration of a specific level of lysis-inhibiting agent wherein the specific level is based upon the apolipoprotein phenotype of the individual. Additionally, the invention yet further relates to methods for enhancing the lysis of coagulated blood by the administration of an Apo E peptide fragment to blood containing a clot lysis agent.

BACKGROUND OF THE INVENTION

Homeostasis is a term known generally to reference a procedure where bleeding or hemorrhage is stopped by either a surgical means or through administration of a coagulation agent. In contrast to many thrombolytic therapies, which administer a clot lysis agent to breakdown or lyse coagulated blood associated with various ischemic diseases, the need to maintain or enhance the coagulation of blood is also a therapeutic and beneficial procedure.

More specifically, the administration of a clot lysis agent such as tissue plasminogen activator (t-PA) within several hours following a stroke is useful in the lysis of blood clots for an individual suffering from an ischemic disease, such as ischemic stroke. If excessive or uncontrollable bleeding results from these therapies, however, it is beneficial to coagulate the blood and/or stop the bleeding. As a result, the administration of a lysis-inhibiting agent may be a beneficial procedure for treating the excessive or uncontrolled bleeding.

This beneficial process can be seen through the process of treating individuals suffering from hemophilia. To treat hemophilia, for instance, many individuals are offered various blood clotting agents and factors to cease or maintain the associated bleeding. Often these individuals, however, develop an insensitivity to these clotting factors, thereby creating the need for new clotting agents to control excessive bleeding.

As undesirable and uncontrollable bleeding can occur in connection with many medical disorders and ischemic diseases, for example, acute stroke, acute myocardial infarction, peripheral arterial occlusion, pulmonary embolism, and venous thrombosis, there is a continuing need to advance and improve current therapeutic treatments in both prophylactic and interventional therapies.

SUMMARY OF THE INVENTION

Accordingly, it is an object of the present invention to provide novel methods for inhibiting the lysis of coagulated blood. It is a further object of the present invention to provide methods for inhibiting the lysis of coagulated blood which may be used in place of prior art therapies.

These and additional objects are provided by the present invention. More particularly, in one embodiment, the invention is directed to methods for inhibiting the lysis of coagulated blood, which methods comprise administering to blood a lysis-inhibiting amount of apolipoprotein E4 (Apo E4) or a therapeutic derivative thereof.

The invention is further directed to methods for reducing the risk of excessive blood clot lysis. These methods comprise administering to blood a lysis-inhibiting amount of Apo E4 or a therapeutic derivative thereof.

In a further embodiment, the invention is directed to methods for inhibiting the lysis of coagulated blood by administering to an individual's blood a specific level of a lysis-inhibiting Apo E4. The specific level of lysis-inhibiting agent to be administered to the individual is based upon the apolipoprotein phenotype of the individual.

In yet a further embodiment, the invention is directed to methods for reducing the risk of excessive blood clot lysis by administering to an individual's blood a specific level of lysis-inhibiting Apo E4 wherein the specific level is based upon the apolipoprotein phenotype of the individual.

In another embodiment, the invention is directed to methods for enhancing the lysis of coagulated blood by administering to blood containing a clot lysis agent an Apo E peptide fragment.

The methods according to the present invention are advantageous to blood coagulation procedures by inhibiting the lysis of coagulated blood and/or reducing the risk of excessive blood clot lysis, particularly in individuals at risk of exhibiting excessive or uncontrollable bleeding. Additionally, these methods are advantageous to blood coagulation procedures by enhancing the lysis of coagulated blood in individuals with excessive blood coagulation by preventing a lysis-inhibiting effect of blood.

These and additional aspects, objects and advantages of the invention are more fully described in the detailed description.

BRIEF DESCRIPTION OF THE DRAWINGS

The following detailed description will be more fully understood in view of the accompanying drawings in which.

DETAILED DESCRIPTION

Figure 1:
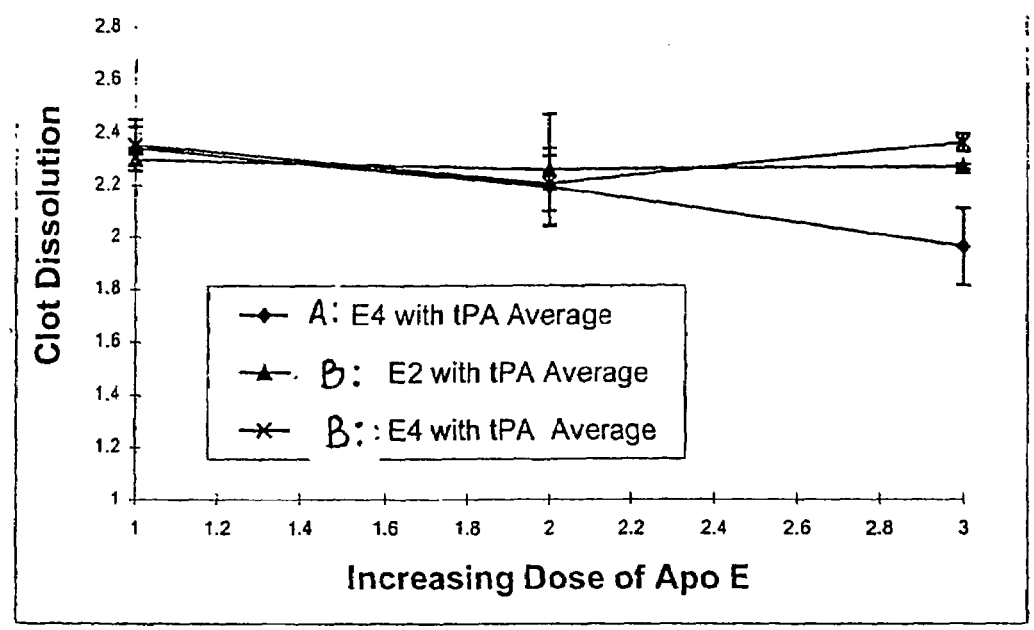
FIG. 1 depicts effects of clot lysis in vitro with respect to t-PA administration in conjunction with increasing doses of Apo E2 or E4, as described in Example 1.

The present invention is directed to methods for inhibiting the lysis of coagulated blood by administering to blood a lysis-inhibiting amount of apolipoprotein E4 (Apo E4) or a therapeutic derivative thereof. This invention also is directed to methods for reducing the risk of undesirable elevated levels of blood clot lysis by administering to an individual's blood a lysis-inhibiting amount of Apo E4 or a therapeutic derivative thereof. Also, the invention is further directed to methods for enhancing the lysis of coagulated blood by administering to blood containing a clot lysis agent an Apo E peptide fragment.

Many current thrombolytic therapies are premised upon the administration of a clot lysis agent to lyse coagulated blood, for example after an ischemic disease is detected. In contrast to the lysis of blood, however, the frequent need to coagulate blood during such procedures or other medically related therapies is crucial when a potential for excessive or uncontrolled bleeding exists. In addition to improving upon previous coagulation therapy procedures, this invention is also directed to methods for inhibiting the lysis of coagulated blood and to methods for reducing the risk of excessive or uncontrollable bleeding by administering a specific level of a lysis-inhibiting amount of Apo E4, wherein the specific level is based upon the apolipoprotein phenotype of the individual to be treated. By determining the apolipoprotein phenotype expressed by an individual, and particularly by determining if an individual expresses Apo E4, a physician or care-giver will be able to predict if inhibition of an administered agent will occur as a result of the individual's inherent phenotype, and therefore more accurately dose the lysis-inhibiting Apo E4 in an amount suitably specific for the individual.

As used herein, "inhibiting the lysis of blood" generally refers to the inhibition, i.e., holding back, i.e., restraining of or reduction in the lysis or breakdown of coagulated blood or blood clots. As used herein, "coagulated blood" generally refers to a clot of blood such that the blood is in the form of a soft semisolid or solid mass. As used herein, "excessive lysis" generally refers to the lysis which is in excess or exceeding the normal level of lytic behavior exhibited by healthy individuals associated with various treatments. "Clot lysis agent" generally refers to any of the known thrombolytic agents which are used to enhance the lysis of blood clots. Known agents include, but are not limited to, TNK-t-PA, t-PA, reteplase, streptokinase, heparin, coumadin, GIIb IIIa receptor blockers, therapeutic derivatives thereof, or mixtures thereof. Preferably, the clot lysis agent comprises tissue plasminogen activator (t-PA) or a derivative thereof.

Apolipoprotein E (Apo E) is known generally as a member of a family of lipid-associated proteins whose isoforms have been implicated as an important modifier of several neurologic, vascular and cardiovascular diseases. See Corder, et al. *Science;* 261:921–3 (1993). Apo E has three common isoforms—E2, E3, and E4. These monomeric isoforms combine to make six Apo E phenotypes: E2/2, E2/3, and E2/4 (referred to as the E2 category), E3/3 (E3 category), and E4/3 and E4/4 (E4 category). See Payami, et al. *JAMA;* 271:1316–7 (1994); Polvikoski, et al. *N Engl J Med;* 333:1242–1247 (1995). Apo E, and its respective isoforms, has been linked to outcome and survival following acute injury of the central nervous system, as well as peripheral cardiovascular system. The presence of an E4 allele has been associated with a poor outcome following severe head trauma and with poorer survival in patients with an intracerebral hemorrhage (ICH). See Alberts et al, *Stoke* 27: 183., 1986; Freidman et al, *Neurology,* 52: 244–248., 1999. The E4 isoforms, E4/3 and E4/4, referred to herein as Apo E4, are employed in the methods of the invention. Therapeutic derivatives can also be administered.

As used herein, "therapeutic derivative" generally refers to an Apo E4 fragment, for example fragments of Apo E4 having the lysis-inhibiting activity, or chemical or structural analogue exhibiting the lysis-inhibiting activity. "Lysis inhibiting amount" generally refers to a quantitative amount of Apo E4 which inhibits lysis activity of blood, with or without a conventional clot lysis agent. Suitable doses of Apo E4, or its therapeutic derivative, necessary to inhibit the lytic activity of a naturally occurring or an administered clot lysis agent such as t-PA will vary depending, inter alia, on physiological characteristics of the individual to be treated, including, but not limited to the Apo E phenotype of the individual, and on the given medical condition of the individual. However, typically, the Apo E4 or derivative is administered in an amount of about equal molar stoicheometry with the clot lysis agent to provide the lytic inhibiting activity. The equimolar amount is based on the amount of clot lysis agent administered, if any, and the amount of clot lysis agent inherent in the blood. For example, human blood typically contains about 0.0009 mg/l t-Pa.

The dosages of conventional clot lysis agents are generally based upon the individual's physiological characteristics and given medical condition. Typically a patient can be administered, for example, a range of t-PA of from about 0.1–10.0 mg/kg of blood. A standard therapeutic dose of t-PA physiologically appropriate for thrombolytic therapy to be administered intravenously to blood over a one hour period is 0.9 mg/kg of blood.

"Ischemic disease" generally refers to a medical condition causing or resulting in a decrease in blood supply to a bodily organ, tissue, or location due to constriction or obstruction of blood vessels. Examples of ischemic diseases comprise myocardial infarction, unstable angina, coronary artery thrombus, and peripheral vascular disease. "Peripheral vascular diseases" typically refers to, inter alia, occlusions, retinopathy, and organ embolisms. "Organ embolism" typically refers to the obstruction or occlusion of a blood vessel by an embolus within an organ system, for example, such as a pulmonary embolism. In treating these and similar ischemic diseases, thrombolytic therapy in the form of a clot lysis agent is often administered to enhance the lysis of coagulated blood. In addition to the need to enhance the lysis of blood, often many medical procedures and thrombolytic therapies may result in excessive bleeding, thereby requiring the administration of a coagulating agent or factor. For instance, some diseases and procedures that may be effected by such thrombolytic therapy and thereby require the administration of a procoagulant include, surgery, vascular surgery, grafts, organ transplants, limb reattachment, trauma pregnancy, child birth, post partum hemophilia, and normal vaginal delivery with excessive post partum bleeding. The methods for inhibiting the lysis of coagulated blood according to the present invention may be employed in treatment of any such diseases or conditions. Additionally, individuals suffering from hemophilia typically require the administration of clotting agents such as Factor VIII to coagulate the blood. Such procedures can also benefit by administering Apo E4 as a clot lysis-inhibiting agent in conjunction with the conventional Factor VIII therapeutic procedures.

In one embodiment, a lysis-inhibiting amount of Apo E4 is administered to an individual with an ischemic disease to inhibit the lysis of coagulated blood associated with the disease.

In a specific embodiment, methods for reducing the risk of excessive blood clot lysis can be administered, particularly in individuals at risk of undesirable or excessive bleeding. These methods comprise administering to blood a lysis-inhibiting amount of Apo E4 or a therapeutic derivative thereof.

In a further embodiment, a specific level of a lysis-inhibiting amount of Apo E4 is administered wherein the specific level is based upon the apolipoprotein phenotype of the individual. In determining the specific level of agent to be administered to the individual, the apolipoprotein phenotype of the individual will help the physician or care-giver conclude how much lysis-inhibiting Apo E4 will be required to obtain desired results. For example, a lesser amount of lysis-inhibiting Apo E4 will typically be required if the individual has an Apo E4 phenotype, due to the clot lysis inhibiting properties exhibited by Apo E4. Preferably, the individual's apolipoprotein phenotype is determined prior to administering the specific level of lysis-inhibiting agent. Methods for determining apolipoprotein phenotype from blood or serum samples are known in the art and may be employed.

In another specific embodiment, the lysis-inhibiting amount of Apo E4 is administered to an individual with post surgical complications of occlusion or clotting to inhibit the lysis of blood clots associated with the ischemic disease. Furthermore, a specific level of a lysis-inhibiting amount of Apo E4 can be administered to an individual based upon the apolipoprotein phenotype of the individual to inhibit the lysis of coagulated blood associated with post surgical complications of occlusion or clotting.

In yet another embodiment, an Apo E peptide fragment is administered to blood containing a clot lysis agent to enhance the lysis of coagulated blood via a competitive antagonist procedure. In administering the Apo E peptide fragment, it is possible to prevent the natural lysis-inhibiting effect of Apo E4 within blood. For example, an Apo E fragment which has functionality for binding with a clot lysis agent but does not exhibit the lysis inhibiting effect of Apo E4 can be administered. As the fragment binds to the clot lysis agent, for example t-PA, it prevents binding of lysis inhibiting Apo E4. The process of competitive inhibition of the inhibition can be used to prevent the natural inhibiting effect of Apo E4 in blood by administering a peptide fragment of Apo E with an associated binding site but without the lysis-inhibiting characteristics. Upon administering this peptide fragment of Apo E into the blood containing Apo E4 and a lysis agent, the structures compete for the same binding site location, thereby allowing some fragments of Apo E to bind to the clot lysis agent prior to Apo E4 binding. As a result, the Apo E peptide fragments protect the blood from receiving the lysis-inhibiting effects associated with the Apo E4 peptides by connecting to the binding site and thereby blocking the Apo E4 interaction. Derivatives through combinational chemistry of the structure, ionic, or electron density map of the Apo E peptide can also be employed as the Apo E fragment to bind to a lysis agent such as t-PA and prevent the lysis-inhibiting effect of the larger molecules of Apo E.

The following example is provided to illustrate the methods and various embodiments of the present invention. While the example below utilizes t-PA as the clot lysis agent for demonstrating the lysis-inhibiting effects of Apo E4, similar results can be obtained with other clot lysis agents as mentioned above. The use of similar clot lysis agents will be apparent to one of ordinary skill in the art and are within the scope of the claims.

EXAMPLE 1

In this example, the lysis-inhibiting effect of Apo E4 is demonstrated in vitro. There are various methods for determining the function, action and or kinetics of t-PA. These include but are not limited to: measuring fibrin degradation fragments, clot lysis, clot weight, fluid evolution weight, clot times and others. Those experienced in the art will be familiar with these and other methods for assaying t-PA activity or clot degradation/formation etc. The data from this study consists of a measurement of clot dissolution or lysis by measuring the amount of liquid liberated from the blood sample. This is an index of clot lysis and the clot lysis is stimulated by t-PA.

Typically, two mls of fresh human blood are drawn and added to pre-weighed vials containing known amounts of t-PA with or without Apo E4. The blood is mixed and allowed to equilibrate for 40 minutes. The vials are centrifuged at 1 g for 15 minutes and the supernatant decanted. Clot weight and solution weight is determined and used to measure clot degradation or dissolution. Increasing supernatant volumes indicate increased clot degradation or increasing clot dissolution.

FIG. 1 depicts the effect of clot lysis on the blood from two individuals with respect to t-PA administration in conjunction with increased dosages of Apo E2 or Apo E4. The y-axis demonstrates in grams (g) the amount of clot lysis or dissolution measured. The administration of t-PA to individual A's blood at a level of 1.0 mg/l blood in conjunction with increasing amounts of Apo E4 shows a dose dependent decrease in clot dissolution. In the top two lines representing individual B's blood, there was no significant change in clot dissolution caused by E4 after administrating t-PA at a level of 0.5 mg/l blood. This is believed to be due to administration of aspirin to the individual prior to sampling. N=3 for each.

Figure 2:
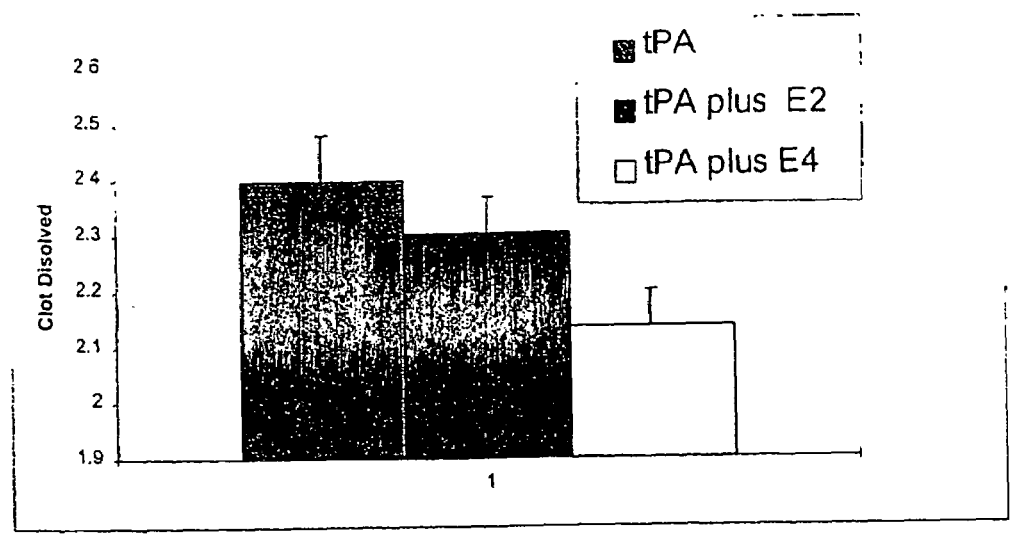
FIG. 2 depicts effects of clot lysis in vitro with respect to t-PA administration in conjunction with Apo E2 or Apo E4 as described in Example 1.

FIG. 2 depicts the effect of clot lysis on additional blood from individual B with respect to t-PA administration in combination with Apo E2 or Apo E4. The y-axis demonstrates in grams (g) the amount of clot lysis or dissolution measured. The administration of t-PA alone at a level of 0.5 mg/l blood shows that the level of clot lysis was substantially complete at 2.5 g. Upon administration of t-PA in conjunction with Apo E2, no significant change in lytic activity was recognized. The amount of clot lysis was significantly inhibited, however, upon the administration of t-PA in conjunction with Apo E4. N=3 for each.

EXAMPLE 2

In this example, the lipophilic interaction of t-PA with Apo E4 is demonstrated through Thin Layer Chromatography (TLC). There are numerous analytical methods for measuring molecular interactions. These are known to those experienced in the art and include, but are not limited to; Thin Layer Chromatography (TLC), Paper Chromatography, electrophoresis, diffraction methods, Nuclear Magnetic Resonance, and other methods.

A known concentration of t-PA in a first prepared solution is applied to a TLC plate and allowed to dry to measure molecular interaction. In a second solution equal molar amounts of t-PA and Apo E4 are employed and the solution is similarly applied to a second TLC plate and allowed to dry.

Figure 3:
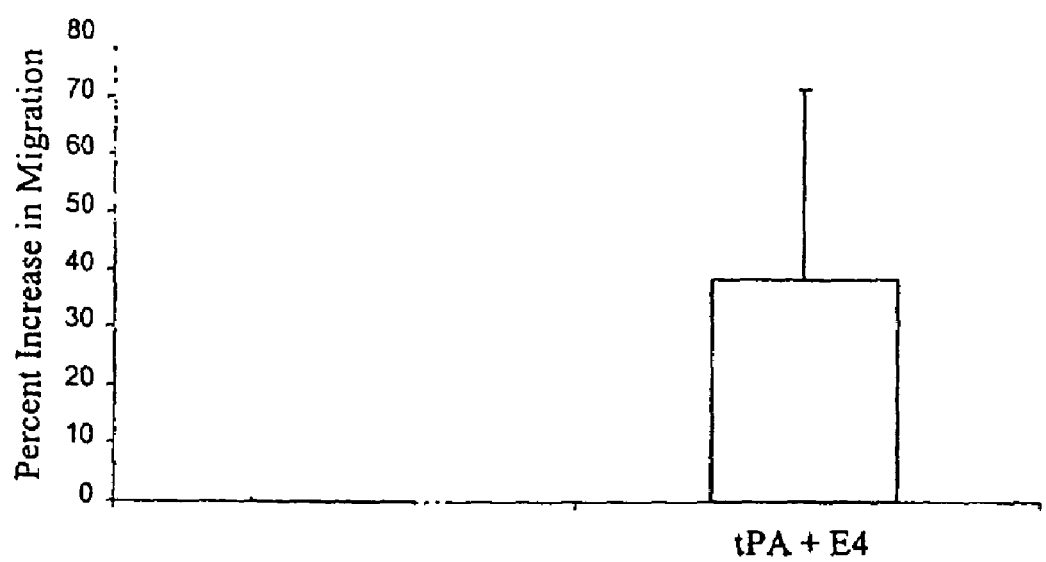
FIG. 3a depicts a lipophilic interaction of t-PA with Apo E4 observed by Thin Layer Chromatography (TLC) as described in Example 2.
FIG. 3b depicts a hydrophobic interaction of t-PA with Apo E4 observed by Thin Layer Chromatography (TLC) as described in Example 3.

The TLC plates are put into migration chambers containing chloroform:ethanol in a 3:1 or 1:1 ratio and allowed to migrate until the solvent front approaches 1 cm from the top of the plate. The plates are removed from the chambers and allowed to dry in the fume cupboards. The plates can be read with ninhydrin or uv light quenching. The migration distances are marked and rf values reported. The plate to which the first solution containing only t-PA is applied is used as a reference and the percent increase in migration exhibited by the second solution is set forth in FIG. 3a, N=3 for each.

The results demonstrate that Apo E4 reacts and uniquely binds with t-PA under the given conditions, presumably through the lipophilic protein properties although the inventors do not intend to be bound by this theory.

EXAMPLE 3

In this example, using an in vitro clot degradation method, the lysis inhibiting effect of Apo E4 on t-PA is further demonstrated. The inhibition of clot dissolution by Apo E4 is statistically significant.

The ability of Apo E isoproteins to modulate t-PA induced clot lysis is assessed using an in vitro clot assay system. This system uses the decrease in clot formation in the presence of t-PA to approximate the amount of clot lysis. Blood samples are obtained from 18 volunteers and divided into three Apo E genotypes (6 patients in each group): E2 (E2/E2, E2/E3, E2/E4), E3 (E3/E3) and E4 (E3/E4, E4/E4). Clot lysis in the presence of varying concentrations of t-PA (0 to 4 μg/ml), is assessed in the presence or absence of supplemental Apo E2, E3 or E4 (9.8 μg/ml) for each patient genotype. The results are expressed as EC50s, which are the effective concentrations of t-PA required to achieve 50% lysis of the clot.

Figure 4:
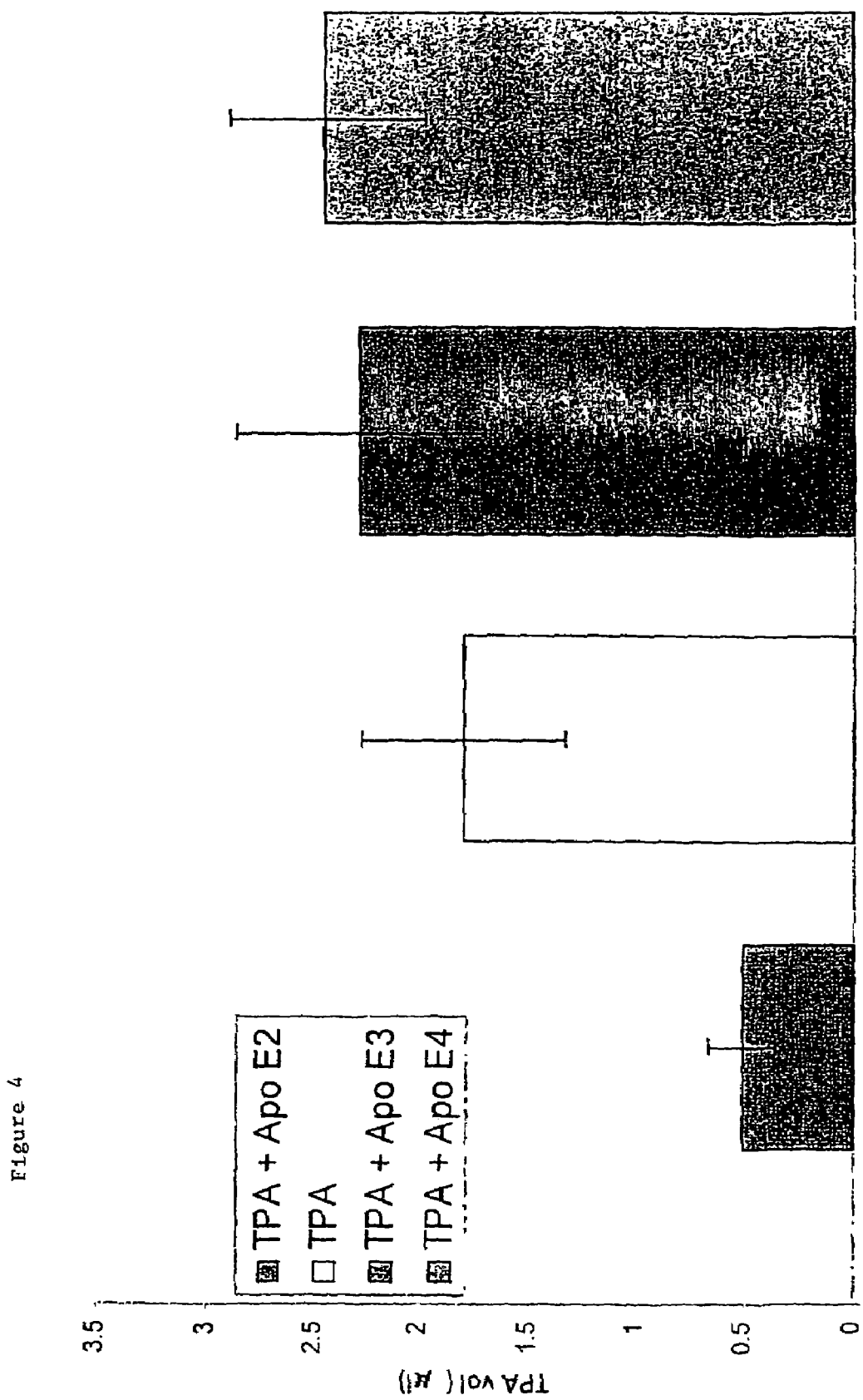
FIG. 4 depicts the average EC50 clot dissolution of t-PA in conjunction with Apo E2, Apo E3 and Apo E4 as described in Example 3.

As shown in FIG. 4, t-PA induced clot lysis is significantly (P±0.0001) enhanced by supplementation with Apo E2 (EC50 of 0.20±0.06 μg/ml) as compared to t-PA alone (0.72±0.19). When Apo E4 is supplemented to the clot lysis assay, there is a significant (P<0.05) inhibition of clot lysis (EC50 of 0.98±0.23 μg/ml) as compared to t-PA alone (0.72±0.19), but there is no significant change in t-PA induced clot lysis caused by Apo. E3. Examining the relationship between patient genotypes and clot lysis, there is a significant increase in clot lysis for all groups with Apo E2 supplementation, and a non-significant trend for the Apo E4 patient group to have decreased clot lysis with Apo E3 and E4 supplementation. The results demonstrate that the t-PA is working through a clot degradation mechanism.

Figure 3B:

Using thin layer chromatography (TLC), as defined in Example 2, Apo E2 and E4 interacted chemically with t-PA, and Apo E3 either did not interact with t-PA or that said interaction is distinctly different than the interaction seen with E2 and E4 (as seen if FIG. 3b). The results demonstrate that Apo E4 reacts and uniquely binds with t-PA under the given conditions, through hydrophobic domains although the inventors do not intend to be bound by this theory.

The specific embodiments and examples set forth above are provided for illustrative purposes only and are not intended to limit the scope of the following claims. Additional embodiments of the invention and advantages provided thereby will be apparent to one of ordinary skill in the art and are within the scope of the claims.

What is claimed is:

1. A method for inhibiting lysis of coagulated blood, comprising administering to blood a lysis-inhibiting amount of apolipoprotein E4 (Apo E4) or a therapeutic derivative thereof.

2. The method as defined by claim 1, wherein the blood comprises a clot lysis agent.

3. The method as defined by claim 2, wherein the clot lysis agent comprises tissue plasminogen activator (t-PA).

4. The method as defined by claim 2, wherein the clot lysis agent comprises a t-PA derivative.

5. The method as defined by claim 2, wherein the clot lysis agent comprises TNK-t-PA, t-PA, reteplase, streptokinase, heparin, coumadin, GIIb IIIa receptor blockers, therapeutic derivatives thereof, or mixtures thereof.

6. The method as defined by claim 1, wherein a therapeutic derivative comprising fragments of Apo E4 having lysis-inhibiting activity is administered.

7. The method as defined by claim 1, wherein the lysis-inhibiting amount of Apo E4 is administered to an individual with an ischemic disease.

8. The method as defined by claim 7, wherein the ischemic disease comprises myocardial infarction, unstable angina, coronary artery thrombus, or peripheral vascular disease.

9. The method as defined by claim 8, wherein the peripheral vascular disease comprises occlusion, retinopathy, or organ embolism.

10. The method as defined by claim 9, wherein the organ embolism comprises pulmonary embolism.

11. The method as defined by claim 1, wherein the lysis-inhibiting amount of Apo E4 is administered to an individual with post surgical complications of occlusion or clotting.

12. A method for reducing risk of excessive blood clot lysis, comprising administering to blood a lysis-inhibiting amount of Apo E4 or a therapeutic derivative thereof.

13. A method for inhibiting lysis of coagulated blood, comprising administering to an individual's blood a specific level of a lysis-inhibiting amount of Apo E4, wherein the specific level is based upon an apolipoprotein phenotype of the individual.

14. The method as defined by claim 13, wherein the apolipoprotein phenotype is Apo E4.

15. The method as defined by claim 13, wherein the blood comprises a clot lysis agent.

16. The method as defined by claim 15, wherein the clot lysis agent comprises tissue plasminogen activator (t-PA).

17. The method as defined by claim 15, wherein the clot lysis agent comprises a t-PA derivative.

18. The method as defined by claim 15, wherein the clot lysis agent comprises TNK-t-PA, t-PA, reteplase, streptokinase, heparin, coumadin, GIIb IIIa receptor blockers, therapeutic derivatives thereof, or mixtures thereof.

19. The method as defined by claim 13, wherein a therapeutic derivative comprising fragments of Apo E4 having lysis-inhibiting activity is administered.

20. The method as defined by claim 13, wherein the individual has an ischemic disease.

21. The method as defined by claim 20, wherein the ischemic disease comprises myocardial infarction, unstable angina, coronary artery thrombus, or peripheral vascular disease.

22. The method as defined by claim 21, wherein the peripheral vascular disease comprises occlusion, retinopathy, or organ embolism.

23. The method as defined by claim 22, wherein the organ embolism comprises pulmonary embolism.

24. The method as defined by claim 13, wherein the lysis-inhibiting amount is administered to an individual with post surgical complications of occlusion or clotting.

25. The method as defined by claim 13, comprising the additional step of determining the individual's apolipoprotein phenotype prior to administering the specific level of lysis-inhibiting Apo E4.

26. A method for reducing risk of excessive blood clot lysis, comprising administering to an individual's blood a specific level of a lysis-inhibiting amount of Apo E4, wherein the specific level is based upon an apolipoprotein phenotype of the individual.

27. The method as defined by claim 26, comprising the additional step of determining the individual's apolipoprotein phenotype prior to administering the specific level of lysis-inhibiting Apo E4.

* * * * *